US006437220B1

(12) United States Patent
Broun et al.

(10) Patent No.: US 6,437,220 B1
(45) Date of Patent: *Aug. 20, 2002

(54) STRONG EARLY SEED-SPECIFIC GENE REGULATORY REGION

(75) Inventors: Pierre Broun, Burlingame; Chris Somerville, Portola Valley, both of CA (US)

(73) Assignees: Monsanto Company, Inc., St. Louis, MO (US); Carnegie Institution of Washington, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/352,125

(22) Filed: Jul. 13, 1999

Related U.S. Application Data

(63) Continuation of application No. 08/898,039, filed on Jul. 18, 1997, now Pat. No. 5,965,793, which is a continuation-in-part of application No. 08/530,862, filed on Sep. 20, 1995, now Pat. No. 6,291,742, and a continuation-in-part of application No. 08/597,313, filed as application No. PCT/US97/02187 on Feb. 6, 1997, now Pat. No. 6,310,194.

(51) Int. Cl.$^7$ .................. C12N 15/29; C12N 15/82; C12N 5/04; A01H 5/00
(52) U.S. Cl. .................. 800/287; 800/281; 800/298; 800/306; 536/23.1; 536/23.6; 536/24.1; 435/69.1; 435/252.3; 435/254.11; 435/257.2; 435/320.1; 435/410; 435/418; 435/419; 435/468
(58) Field of Search .................. 536/23.1, 23.6, 536/24.1; 435/69.1, 252.1, 252.3, 320.1, 410, 418, 419, 468, 471, 254.11, 257.2; 800/278, 281, 287, 306

(56) References Cited

U.S. PATENT DOCUMENTS

| | | | |
|---|---|---|---|
| 5,057,419 A | 10/1991 | Martin et al. ................ | 435/134 |
| 5,443,974 A | 8/1995 | Hitz et al. ................ | 435/172.3 |
| 5,475,099 A | 12/1995 | Knauf et al. ................ | 536/23.6 |
| 5,487,991 A | 1/1996 | Vandekerckhove et al. | |
| 5,530,186 A | 6/1996 | Hitz et al. ................ | 800/264 |
| 5,530,194 A | 6/1996 | Knauf et al. ................ | 800/264 |
| 5,543,576 A | 8/1996 | van Ooijen et al. ...... | 800/317.3 |
| 5,552,306 A | 9/1996 | Thomas et al. ............. | 435/134 |
| 5,559,223 A | 9/1996 | Falco et al. ................. | 800/278 |
| 5,589,619 A | 12/1996 | Chappel et al. ............. | 800/278 |
| 5,965,793 A | * 10/1999 | Broun et al. ................ | 800/287 |

OTHER PUBLICATIONS

Benfy et al., 1990, The Cauliflower Mosaic Virus 35S promoter: combinatorial regulation of transcription in plants, Science, vol. 250:959–966.*
Kim et al., 1994, A 20 nucleotide upstream element is essential for the nopaline synthase (nos) promoter activity, Plant Molecular Biology, vol. 24: 105–117.*

Van De Loo et al., "An Oleate 12–Hydroxylase From *Ricinus Communis* L. Is A Fatty Acyl Desaturase Homolog", Proc. Natl. Acad. Sci., vol. 92, 1995, pp 6743–6747.
Okuley et al., "Arabidopsis FAD2 Gene Encodes The Enzyme That Is Essential For Polyunsaturated Lipid Synthesis", The Plant Cell., vol. 6, 1994, pp 147–158.
Broun et al., Accumulation of Ricinoleic, Lesquerolic, and Densipolic Acids in Seeds of Transgenic Arabidopsis Plants That Express a Fatty Acyl Hydroxylase cDNA from Castor Bean, Plant Physiol. (1997) 113:933–942.
Broun et al., A bifunctional oleate 12–hydroxylases: desaturase from *Lesquerella fendleri*, The Plant Journal (1998) 13(2), 201–210.
Altshul et al. J. Mol Biol., 215:403–410 (1990).
Arondel et al. Science, 258: 1353–1355 (1992).
Atsmon et al. Castor, McGraw–Hill, New York pp. 438–447 (1989).
Bafor et al. Biochem., 280:507–514 (1991).
Battey et al. Plant Physiol., 90:835–840 (1980).
Bechtold et al. C.R. Acad. Sci. Paris, 316:1194–1199 (1993).
Beltz et al. Methods in Enzymology, 100:266–285 (1983).
Bray et al. Planta, 172:364–370 (1987).
Browse et al, Ann. Rev. Plant Physiol. Plant Mol. Biol., 42:467–506 (1991).
Canvin, Can. J. Biochem. Physiol., 41:1879–1885 (1963).
Carlson et al, J. Am. Oil Chem. Soc., 67:438–442 (1990).
Ditta et al, Proc. Natl. Acad. Sci. USA, 77:7347–7351 (1980).
Fox et al, Proc. Natl. Acad. Sci. USA, 90:2486–2490 (1993).
Gilliard et al, J. Biol. Chem., 241:5806–5812 (1966).
Gibson et al., Plant Physiol., 106: 1615–1621 (1994).
Gould et al., Proc. Natl. Acad. Sci. USA, 86:1934–1938 (1989).
Greenwood et al. Can. J. Bot., 60:1751–1760 (1982).
Gunstone et al., The Lipid Handbook, Chapman and Hall, London, Chapters 1.9, pp. 19–20 and 3.3.5, pp. 57–58.
Howling et al., Biochim. Biophys. Acta, 260:10–19 (1972).
Huynh et al., DNA Cloning, vol. 1: A Practical Approach, (ed) D.M. Glover, IRL Press, Washington, D.C., pp. 49–77 (1985).
Iba et al., J. Biol. Chem., 268:24099–24105 (1993).
James et al., Biochem. J., 95:448–452 (1965).
Jones et al., Transgenic Res., 1:285–297 (1992).
Kearns et al., Arch. Biochem. Biophys., 284:431–436 (1991).

(List continued on next page.)

Primary Examiner—Elizabeth F. McElwain
Assistant Examiner—Cynthia Collins
(74) Attorney, Agent, or Firm—Morgan, Lewis & Bockius LLP

(57) ABSTRACT

Nucleic acid sequences and methods for their use are described which provide for early seed-specific transcription, in order to modulate or modify expression of foreign or endogenous genes in seeds, particularly embryo cells. The method finds particular use in conjunction with modifying fatty acid production in seed tissue.

19 Claims, 7 Drawing Sheets

OTHER PUBLICATIONS

Knuzton et al. Proc. Natl. Acad. Sci. USA, 89:2624–2628 (1992).
Kok et al. J. Biol. Chem., 264:5435–5441 (1989).
Konez et al. Mol. Gen. Genet., 204:383–396 (1986).
Kren et al. Experentia, 41:1476–1477 (1985).
Matzke et al., Plant Physiol. 107: 679–685, (1995).
Miquel et al. J. Biol. Chem., 267:1502–1509 (1992).
Moreau et al. Plant Physiol., 67:672–676 (1981).
Morris, Biochem. Biophys. Res. Commun., 29:311–315 (1967).
Morris, Biochem. J., 118:681–693 (1970).
Morris et al., Biochem. J., 100:29c–30c (1966).
Murray et al. Nucl. Acids Res., 8:4321–4325 (1980).
Newman et al. Plant Cel, 5:701–714 (1993).
Okuley et al. Plant Cell, 6:147–158 (1994).
Ooms et al. Plasmid, 7:15–29 (1982).
Panaccione et al. Gene, 86:163–170 (1990).
Prasad et al. J. Am. Oil Chem. Soc., 64:1424–1427 (1987).
Puissant et al. BioTechniques, 8:148–149 (1990).
Sambrook et al. Molecular Cloning: A Laboratory Manual, 2nd ed., Cold Spring Harbor Laboratory Press (1989).
Schmidt et al. Am. Soc. Plant Physiol., pp. 40–49 (1993).
Shanklin et al. Biochemistry, 33: 12787–12794, (1994).
Smith, Fatty Acids, Pryde E.H., Ed., American Oil Chemists' Society, Champaign, 2nd ed., pp. 29–47.
Smith et al. Biochem. J., 287:141–144 (1992).
Suzuki et al. J. Bacteriol., 173:1690–1695 (1991).
Thiede et al. J. Biol. Chem. 261:13230–13235 (1986).
Topfer et al., Science 268: 681–686 (1995).
van de Loo et al. Lipid Metabolism in Plants, T.S. Moore Jr., Ed. CRC Press, Boca Raton, pp. 91–126 (1993).
van de Loo et al. Plant Physiol., 105:443–444 (1994).
van de Loo et al. Proc. Natl. Acad. Sci. USA, 92:6743–6747 (1995).
von Heijne, J. Mol. Biol., 184:99:105 (1985).

* cited by examiner

FIG. 3A

```
              10         20         30         40         50
        AAGCTTTTGA GCTCATCAGT TACTCAGGAA GATTAAGTCT TTGCTTGTTG
        HindIII
              60         70         80         90        100
        TCTGATTTTC TTTAAATACA TGAAGGATCG GTTATGAATC TTCTTTTTTT
             110        120        130        140        150
        GTGTTTTGGG ATTATGAAGC TGTCTTTGGA TATTAGTTGC GGTTATTAGC
             160        170        180        190        200
        ATGCTTCTCT TTTGTGTTTT GGGGATTATG AAGCAGGGTC TGTCTATGTA
             210        220        230        240        250
        ATGCATTTTG TTTGAAAACT CAGCTAATGC TAATGCAATT TCTTTTGAAA
             260        270        280        290        300
        CCTTTGTTAT GTTTCGAAA  ATATTGAATA NGTTCTGTTA TGGATTTATT
             310        320        330        340        350
        TGCAAAAGCC ATTGATTAAA TCAAACATTA CATAAGAACA ACATTCATTA
             360        370        380        390        400
        TTAACTAATT AGAGATGCAA AACACAACAT TACATACAAC ATCAGTGACT
             410        420        430        440        450
        AATTATTGAG ACAAACAAC  ATCACATACA CAAACATTCA TCTCATACAT
             460        470        480        490        500
        CACTTAGAGA GACACAAAAA GCAACCAAAC ACAACTATTC CGGCAACAAC
             510        520        530        540        550
        AATTAGCTTC ATACGTTTTG CTTCTCCTTT CAAGCCTTCA ATCATCTTCT
             560        570        580        590        600
        CACAGCCACG AATCTGAGCC TTCAATAATA ACATTTCTTC ATCGTGACAC
             610        620        630        640        650
        TTCTCACGGT TATGAATGTA AGCCTTTATG TCCTCTACTT CTTCTACTAA
             660        670        680        690        700
        AGACACATCA GTCCACTTCC AGGTGTGGAA TCCTCCTCTT TTGAAATTTT
             710        720        730        740        750
        TCTCACAGGT ATGGAATAAT CTACCTAGGT TTTTTGGAGT TCTTGAGGTT
             760        770        780        790        800
        CTGATCACAA CACGACATCC AAATCGACAG GTCTTAGGAA AACCACGATG
             810        820        830        840        850
        GTTATCATCT TCAAGCTCAC TGTCAAAAGA GAAAAACGAG TTTGAAGAAG
             860        870        880        890        900
        AAGAAGGCAT TATCAATTTC AGAGAATTTT GGAGAATTTT GAGAGATTGA
             910        920        930        940        950
        GAATTGGGAA ATAAGAACCC TAATCCCCAA TTTATGAGAT TGAAAATATA
             960        970        980        990       1000
        TCCGTTAGAG AAGAAACATA ATGCTGTGCG TTTTAATTAG AAAAAATAGA
            1010       1020       1030       1040       1050
        GATGGGCTTT ATCTTTTGTT AAGAGTTTTG GGCTTGGGCT TGGGTTTTTG
            1060       1070       1080       1090       1100
        ATAAAAAAAT TTAATTAAAC CAAAACGACG TCGTTTGGTT TAATTGTTGT
            1110       1120       1130       1140       1150
        TAAAAAAAAT TAAAACACCA AAACGACGTC GTTTTGGTGT TATTAACGGC
            1160       1170       1180       1190       1200
        CTTAAAACGG ATTAAATCCA TAATCCGTCA GTCAACTAGG TTACGGATGG
            1210       1220       1230       1240       1250
        TCAACGGCGT TTTTGCATAA CGGAGGCACA GTTCAGGCTT AACGGAGTGG
```

FIG. 3B

```
           1260        1270        1280        1290        1300
      ACCGAATGGC  TTTTTAGGAA  GTTTGTAACC  GGGATTTTTT  GTTTATGATG
           1310        1320        1330        1340        1350
      TATTTGTCCC  CGTCGGCTAT  TGTTTAGGCC  GTTTTTCCTA  TATATTGGAA
           1360        1370        1380        1390        1400
      ATAACTATTG  TCCAGACGAG  TTACTTCTCC  AACATATCAA  GAAATGTTAC
           1410        1420        1430        1440        1450
      AAAGAAGTGT  TACAAAAATG  TGTTACTAAG  CCATAAAACT  CAAAGCATAT
           1460        1470        1480        1490        1500
      ATCTTAGACC  CTAAGCCTAA  ACCCTAGAAC  TTTCTAGGAC  GTTTATACCT
           1510        1520        1530        1540        1550
      TGTCCTTTCT  TTAGTTTCCT  TTAAAGGCCT  TCGTATTCAT  AAGTTTTATT
           1560        1570        1580        1590        1600
      TTTGCTTAAT  ACTAACACTA  GAAATAATCA  ACATAAACTA  GGTTAAGTCG
           1610        1620        1630        1640        1650
      TGGATCTAAT  TTTATTGTGA  AAATGTAATT  GCTTCTCTTA  AGAAAAGATT
           1660        1670        1680        1690        1700
      CATAGCAAAA  TATTCGCATC  TTTCTTGTGA  ATCATCTTTT  GTTTTTGGGG
           1710        1720        1730        1740        1750
      CTATTAAAGA  AAAATTGAAC  TCATGAAATG  GTGACAACTT  TATTCTAGAG
           1760        1770        1780        1790        1800
      GTAACAGAAC  AAAAATATAG  GAACAACACG  TGTTGTTCAT  AAACTACACG
           1810        1829        1830        1840        1850
      TATAATACTC  AAGAAGATGA  ATCTTTATAA  GAATTTAGTT  TTCTCATGAA
           1860        1870        1880        1890        1900
      AACATAAAAA  ATTTTGTCAA  TTGAAAGTGA  CAGTTGAAGC  AAAGGAACAA
           1910        1920        1930        1940        1950
      AAGGATGGTT  GGTGATGATG  CTGAAATGAA  AATGTGTCAT  TCATCAAATA
           1960        1970        1980        1990        2000
      CTAAATACTA  CATTACTTGT  CACTGCCTAC  TTCTCCTATT  TCCTCCGCCA
           2010        2020        2030        2040        2050
      CCCATTTTGG  ACCCACGAGC  CTTCCATTTA  AACCCTCTCT  CGTGCTATTC
           2060        2070        2080        2090        2100
      ACCAGAAGAG  AAGCCAAGAG  AGAGAGAGAG  AGATTGTGCT  GAGGATCATT
           2110        2120        2130        2140        2150
      GTCTTCTTCA  TCGTTATTAA  CGTAAGTTTT  TTTTGACCAC  TCATATCTAA
           2160        2170        2180        2190        2200
      AATCTAGTAC  ATGCAATAGA  TTAATGACTG  TTCCTTCTTT  TGATATTTTC
           2210        2220        2230        2240        2250
      AGCTTCTTGA  ATTCAAGATG  GGTGCTGGTG  GAAGAATAAT  GGTTACCCCC
                    EcoRI
           2260        2270        2280        2290        2300
      TCTTCCAAGA  AATCAGAAAC  TGAAGCCCTA  AAACGTGGAC  CATGTGAGAA
           2310        2320        2330        2340        2350
      ACCACCATTC  ACTGTTAAAG  ATCTGAAGAA  AGCAATCCCA  CAGCATTGTT
           2360        2370        2380        2390        2400
      TCAAGCGCTC  TATCCCTCGT  TCTTTCTCCT  ACCTTCTCAC  AGATATCACT
           2410        2420        2430        2440        2450
      TTAGTTTCTT  GCTTCTACTA  CGTTGCCACA  AATTACTTCT  CTCTTCTTCC
           2460        2470        2480        2490        2500
      TCAGCCTCTC  TCTACTTACC  TCGCTTGGCC  TCTCTATTGG  GTATGTCAAG
```

FIG. 3C

```
       2510       2520       2530       2540       2550
  GCTGTGTCTT AACCGGTATC TGGGTCATTG GCCATGAATC TGGTCACCAT
       2560       2570       2580       2590       2600
  GCATTCAGTG ACTATCAATG GGTAGATGAC ACTGTTGGTT TTATCTTCCA
       2610       2620       2630       2640       2650
  TTCCTTCCTT CTCGTCCCTT ACTTCTCCTG GAAATACAGT CATCGTCGTC
       2660       2670       2680       2690       2700
  ACCATTCCAA CAATGGATCT CTCGAGAAAG ATGAAGTCTT TGTCCCACCG
       2710       2720       2730       2740       2750
  AAAAAAGCTG CAGTCAAATG GTATGTTAAA TACCTCAACA ACCCTCTTGG
       2760       2770       2780       2790       2800
  ACGCATTCTG GTGTTAACAG TTCAGTTTAT CCTCGGGTGG CCTTTGTATC
       2810       2820       2830       2840       2850
  TAGCCTTTAA TGTATCAGGT AGACCTTATG ATGGTTTCGC TTCACATTTC
       2860       2870       2880       2890       2900
  TTCCCTCATG CACCTATCTT TAAAGACCGA GAACGCCTCC AGATATACAT
       2910       2920       2930       2940       2950
  CTCAGATGCT GGTATTCTAG CTGTCTGTTA TGGTCTTTAC CGTTACGCTG
       2960       2970       2980       2990       3000
  CTTCACAAGG ATTGACTGCT ATGATCTGCG TCTATGGAGT ACCGCTTTTG
       3010       3020       3030       3040       3050
  ATAGTGAACT TTTTCCTTGT CTTGGTAACT TTCTTGCAGC ACACTCATCC
       3060       3070       3080       3090       3100
  TTCGTTACCT CATTATGATT CAACCGAGTG GGAATGGATT AGAGGAGCTT
       3110       3120       3130       3140       3150
  TGGTTACGGT AGACAGAGAC TATGGAATAT TGAACAAGGT GTTCCATAAC
       3160       3170       3180       3190       3200
  ATAACAGACA CACATGTGGC TCATCATCTC TTTGCAACTA TACCGCATTA
       3210       3220       3230       3240       3250
  TAACGCAATG GAAGCTACAG AGGCGATAAA GCCAATACTT GGTGATTACT
       3260       3270       3280       3290       3300
  ACCACTTCGA TGGAACACCG TGGTATGTGG CCATGTATAG GGAAGCAAAG
       3310       3320       3330       3340       3350
  GAGTGTCTCT ATGTAGAACC GGATACGGAA CGTGGGAAGA AAGGTGTCTA
       3360       3370       3380       3390       3400
  CTATTACAAC AATAAGTTAT GAGGCTGATA GGGCGAGAGA AGTGCAATTA
       3410       3420       3430       3440       3450
  TCAATCTTTT TTTCATGTTT TAGGTGTCTT GTTTAAGAAG CTATGCTTTG
       3460       3470       3480       3490       3500
  TTTCAATAAT CTCAGAGTCC ATTTAGTTGT GTTCTGGTGC ATTTTGCCTA
       3510       3520       3530       3540       3550
  GTTATGTGGT GTCGGAAGTT AGTGTTCAAA CTGCTTCCTG CTGTGCTGCC
       3560       3570       3580       3590       3600
  CAGTGAAGAA CAAGTTTACG TGTTTAAAAT ACTCGGAACG AATTGACCAC
       3610       3620       3630       3640       3650
  AANATATCCA AAACCGGCTA TCCGAATTCC ATATCCGAAA ACCGGATATC
       3660       3670
  CAAATTTCCA GAGTACTTAG
```

STRONG EARLY SEED-SPECIFIC GENE REGULATORY REGION

CROSS-REFERENCE TO RELATED APPLICATIONS

This application is a continuation of application Ser. No. 08/898,038, filed Jul. 18, 1997, now U.S. Pat. No. 5,965,793 which is a continuation-in-part of application Ser. No. 08/530,862, filed Sep. 20, 1995, now U.S. Pat. No. 6,291,742; application Ser. No. 08/597,313, filed Feb. 6, 1996, now U.S. Pat. No. 6,310,194 and application Ser. No. PCT/US97/02187, filed Feb. 6, 1997.

GOVERNMENT RIGHTS

The invention described herein was made in the course of work under grant number DE-FG02-94ER20133 from the U.S. Department of Energy. Therefore, the U.S. Government may retain certain rights in this invention.

INTRODUCTION

1. Technical Field

A transcription regulatory region, comprising a nucleotide sequence, which promotes early seed-specific transcription of contiguous nucleotide sequences is provided.

2. Background

A large number of genes are known which are expressed only in developing seeds, or are expressed in developing seeds at much higher levels than in any other organ or tissue type. For the purposes herein, "gene expression" refers to synthesis of mRNA corresponding to a given gene. Thus, the amount of gene expression generally refers to the rate of transcription, or the rate of synthesis of the mRNA. For convenience, in the context of this invention, we have generally assumed that differences in the steady-state level of mRNA accumulation reflects differences in the rate of synthesis of the mRNA. It is understood that in some cases changes in the steady-state level of mRNA could be caused by changes in the rate of mRNA degradation. However, it is considered unlikely that manipulation of promoter sequences, as taught herein, will generally affect the rate of mRNA degradation.

Much of the information about seed-specific gene expression has been derived from studies of genes encoding storage proteins (reviewed by Bevan et al., 1993). For instance, DNA sequences that confer embryo-specific expression by the soybean conglycinin promoter in transgenic plants have been identified (Chen et al., 1988). Similarly, the storage protein napin is one of the major protein components of *Brassica napus* L. (oilseed rape) seeds. A 152 bp fragment from the napin promoter directed strong expression of the β-glucuronidase reporter gene in mature tobacco seeds (Stalberg et al., 1996). Thus, the sequences that direct strong seed-specific expression of storage proteins are conserved between distantly related plant species. The napin promoter has been used to control expression of genes in transgenic plants designed to produce novel fatty acids (e.g., Voelker et al., 1996). However, because storage lipid accumulation begins substantially before the maximal level of expression of the napin or other storage protein genes is reached (Post-Beittenmillar et al., 1992), the promoters of storage protein genes may not be preferred for controlling expression of genes related to storage lipid accumulation.

In the present invention, a preferred regulatory region (e.g., promoter, enhancer, silencer) for expression of genes directed toward modification of seed lipid composition, or other applications, would be derived from a gene that has a similar, or identical, temporal and tissue-specific pattern of expression to the genes that encode enzymes involved in seed storage lipid synthesis and accumulation. However, until recently, relatively few genes were known which are involved in lipid metabolism and are expressed in seed-specific manner. The kappa hydroxylase from the Crucifer *Lesquerella fendleri* is one of the first examples of this class of genes. A promoter of the present invention normally controls the expression of the kappa hydroxylase from *L. fendleri*. Kappa hydroxylase is thought to be located in the endoplasmic reticulum where it catalyzes the introduction of a hydroxyl group into fatty acids attached to the sn-2 position of phospholipids. Since hydroxylated fatty acids are abundant in the seed storage lipids of *L. fendleri* but are not found to any appreciable extent in other organs or tissues, it seems likely that the gene is only expressed appreciably in seeds. The isolation of the kappa hydroxylase gene from *L. fendleri* was described in U.S. patent application Ser. Nos. 08/530,862 and 08/597,313, and PCT/US97/02187. Evidence was presented showing that the mRNA for the kappa hydroxylase was abundant in seeds but was not detectable in vegetative tissues. Here, we demonstrate that a regulatory region in the 5' direction from the coding sequence of the *L. fendleri* kappa hydroxylase is useful as a seed-specific promoter in plant species other than *L. fendleri*. We also show that the regulatory region can be used to cause early seed-specific expression of a gene other than the kappa hydroxylase (i.e., heterologous gene expression) Regulatory regions having the desired properties described herein should also be found upstream of other plant fatty acyl hydroxylase genes isolated and identified as disclosed in the parent applications.

SUMMARY OF THE INVENTION

It is an object of the present invention to provide a transcription regulatory region for use in transgenic plants that exhibits seed-specific expression of a gene product.

It is a further object of the present invention to provide a transcription regulatory region for use in transgenic plants that exhibits an early level of expression of a gene product in developing seeds.

It is yet another object of the present invention to provide a transcription regulatory region for use in transgenic plants that exhibits high-level expression of a gene product.

Isolated nucleic acids (e.g., DNA, RNA, cDNA, cRNA) are provided that comprise a transcription regulatory region (e.g., promoter, enhancer, silencer) from a plant fatty acyl hydroxylase gene. Preferably, the plant gene is a kappa hydroxylase gene and, more preferably, the kappa hydroxylase gene is from Lesquerella. The regulatory region may comprise a nucleotide sequence from SEQ ID NO:1. The regulatory region may comprise between about 500 nucleotides to about 2000 nucleotides, and may be capable of directing expression at a high level, at an early stage of development, in a seed-specific manner, or a combination thereof. The isolated nucleic acid may further comprise a sequence encoding for the native fatty acyl hydroxylase.

Recombinant nucleic acids (e.g., DNA, RNA, cDNA, cRNA) are provided that are comprised of the isolated nucleic acid described above and an operably linked non-native sequence to be transcribed. The sequence may be from the same plant species from which the regulatory region is derived or from a different species or genera; the sequence may even be from a bacterial, fungal, or mammalian gene. Preferably, the sequence is derived from a plant gene, especially one that is involved in seed lipid metabolism or seed development. The sequence may be in the sense or antisense orientation relative to transcription.

Expression constructs (e.g., DNA, RNA, cDNA, CRNA) are provided which are employed in manipulating plant cells to provide for early and/or seed-specific transcription. In particular, transcription regulatory regions from a gene encoding a fatty acyl hydroxylase are operably linked to other than the native or homologous gene, and introduced into a plant cell host for integration into the genome to provide for early and/or seed-specific transcription. The constructs provide for modulation of expression of endogenous products as well as production of exogenous products in the seed.

Transformed host cells, transgenic plants, and transgenic seeds are provided that contain an integrated or non-integrated nucleic acid, recombinant nucleic acid, or expression construct as described above. The host cell may be of bacterial, fungal, plant, animal, or similar origin. The transgenic plant may be Arabidopsis, Brassica, cotton, soybean, safflower, sunflower, tobacco, flax, peanut, or any other dicot species in which early seed-specific gene expression is desired. The regulatory region of the invention may also be useful in controlling seed-specific expression of genes in monocotyledonous species such as wheat, maize, rice, or the like. Transgenic seeds may be derived from similar plant species. Oil may be pressed, or otherwise extracted, or other materials such as proteins, carbohydrates, polyalkanoates, or secondary metabolites may be extracted from the transgenic seed.

Kits are also provided containing a nucleic acid, recombinant nucleic acid, expression construct, host cell, or a combination thereof with directions for the use of the aforementioned to produce a transgenic plant or seed.

BRIEF DESCRIPTION OF THE DRAWINGS

FIG. 3 shows a partial nucleotide sequence of genomic clone pLesqtot containing the promoter region and coding region of the kappa hydroxylase gene from *L. fendleri*. The clone (3670 bp of continuous nucleotide sequence, SEQ ID NO:1) encodes a 2217 bp 5' untranslated region (i.e., sequence preceding the initiating ATG codon), an 1152 bp open reading frame, and a 302 bp 3' untranslated region. The HindIII and EcoRI sites used in subcloning are indicated with double underlines. The ATG that corresponds to the first translated codon of the kappa hydroxylase is underlined.

DETAILED DESCRIPTION OF THE INVENTION

Figure 1:
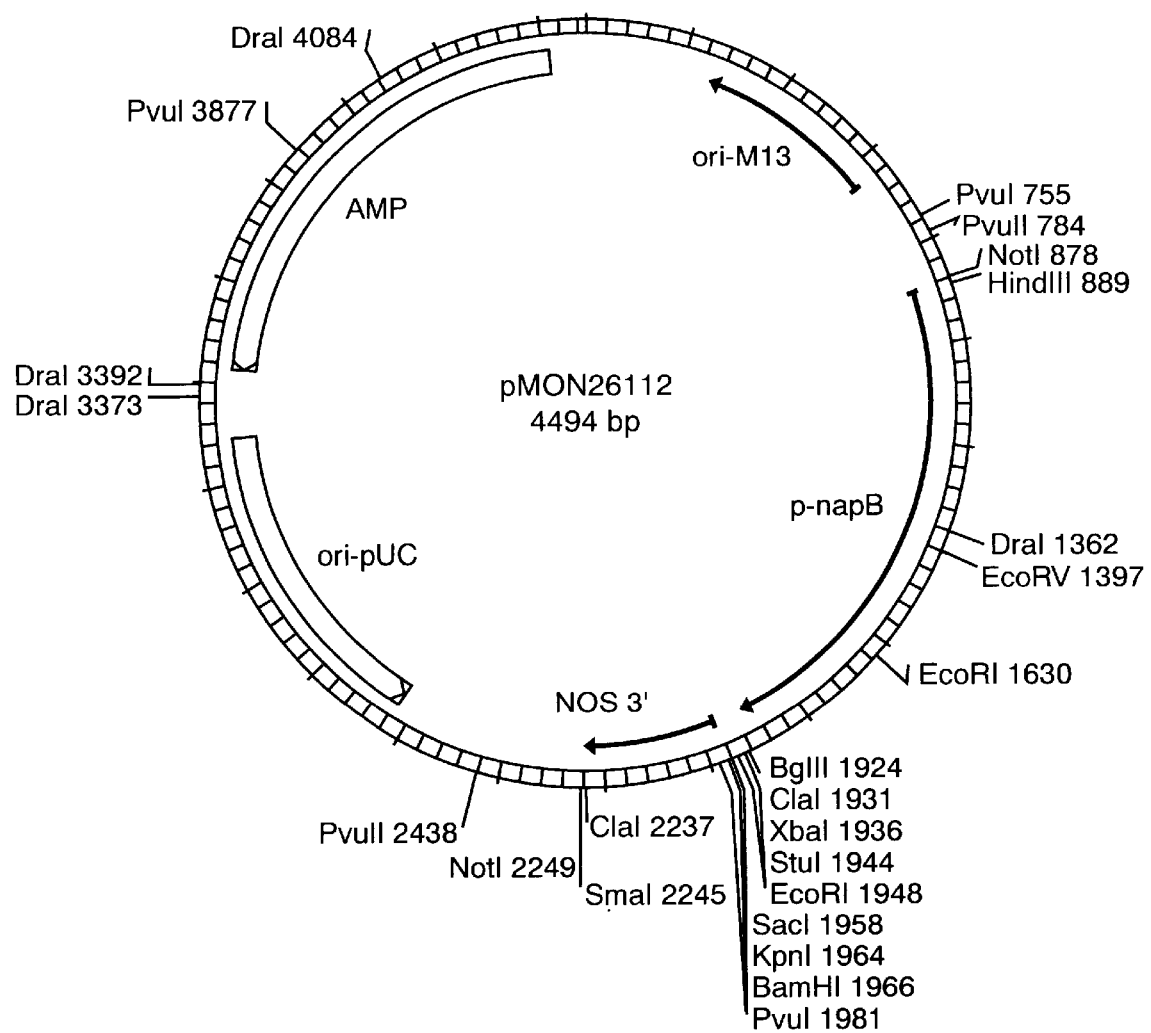
FIG. 1 is a restriction map of plasmid pMON26112.

In accordance with the subject invention, expression constructs are provided which allow for modification of transcription in seeds, particularly in embryos during seed maturation. The expression constructs comprise a regulatory region (e.g., promoter, enhancer, silencer) associated with seed formation, preferably in association with embryogenesis and seed maturation.

Downstream from and under the transcriptional regulation of the kappa hydroxylase regulatory region will be a sequence of interest which will provide for modification of the phenotype of the seed, by modulating the production of an endogenous product, as to amount, relative distribution, timing or the like, or production of an exogenous expression product to provide for a novel function or product in the seed. The construct will preferably provide for a polyadenylation and/or a termination region, so as to provide an expression cassette into which a gene may be introduced.

Conveniently, transcriptional initiation and termination regions may be provided separated in the direction of transcription by a linker or polylinker having one or a plurality of restriction sites for insertion of the gene to be under the transcription regulation of the regulatory region (s). Usually, the linker will have from 1 to 10, more usually from about 1 to 8, preferably from about 2 to 6 restriction sites. Generally, the linker will be fewer than 100 bp, frequently fewer than 60 bp and generally at least about 5 bp. For an insert generated by nucleic acid amplification, the insert may be linked to a regulatory region by techniques such as, for example, restriction enzyme digestion, direct blunt-end ligation, ligation-independent cloning (LIC), and ligation to a single 3'-overhang of a thymidine residue (U.S. Pat. No. 5,487,993).

The transcription regulatory region of this invention may be foreign, or heterologous to the host. By foreign is intended that the regulatory region is not found in the host into which the regulatory region is introduced. Of particular interest are those transcription regulatory regions associated with the seed-specific kappa hydroxylase gene, especially that of *L. fendleri*.

A transcription regulatory region may be used for varying the phenotype of seeds. Various changes in phenotype are of interest. These include modifying the fatty acid composition in seeds, that is changing the ratio and/or amounts of the various fatty acids, as to length, unsaturation, hydroxlation, epoxidation, or the like. Thus, the fatty acid composition may be varied by introducing enzymes which modify the fatty acids to produce fatty acids which are not normally found in the host plant. It may also be desirable to use the promoter of this invention to produce proteins that are directly useful in their own right, such as proteins that have catalytic properties for industrial use. Alternatively, one may provide various products from sources other than plants such as, for example, mammals, fungi, archaeabacteria, and eubacteria. Indeed, the transcriptional initiation region of this invention may be generally used to produce any protein of interest in a seed of a plant host.

An expression cassette may include in the 5'→3' direction of transcription, a transcriptional initiation region, a nucleotide sequence of interest, and a transcriptional termination region functional in plants. In many, but not all, cases the expression cassette may also include translation initiation and termination sequences (i.e. a transcriptional/translational cassette). One or more introns may also be present.

The nucleotide sequence may usually have any open reading frame encoding at least part of a peptide of interest (e.g., an enzyme), or a sequence complementary to a genomic sequence (e.g., antisense), where the genomic sequence may be an open reading frame, an intron, a non-coding leader sequence, or any other sequence where the complementary sequence will inhibit transcription, messenger RNA processing (e.g., splicing), or translation. The nucleotide sequence of interest may be synthetic, naturally derived, or a combination thereof; the nucleic acid may be purified from a natural source (e.g., bacteria), a reaction mixture comprising template and a polymerase (producing DNA, cDNA or cRNA), or chemical synthesis.

In preparing the expression cassette, the various nucleotide fragments may be manipulated, so as to provide for nucleotide sequences in the proper orientation and, as appropriate, in the proper reading frame. Towards this end, adapters or linkers may be employed to join the nucleotide fragments or other manipulations may be involved to provide for convenient restriction sites, removal of superfluous nucleotides, removal of restriction sites, or the like. For this purpose, in vitro mutagenesis, primer repair, restriction, annealing, resection, ligation, or the like may be employed, where insertions, deletions, inversions, or substitutions (e.g., transition, transversion), may be involved.

The termination region which is employed will be primarily chosen for convenience, since the termination regions appear to be relatively interchangeable. The termination region may be native to the transcriptional initiation region, may be native to the nucleotide sequence of interest, or may be derived from another source. Convenient termination regions are available from the Ti-plasmid of *A. tumefaciens*, such as the octopine synthase and nopaline synthase termination regions.

The nucleic acids and constructs of the invention may further comprise sequences that permit propagation and selection of the constructs in a foreign host. Optionally, an origin of replication and a selectable marker may be included in the nucleic acid or construct. The origin of replication would preferably be derived from a microbe (e.g., bacteria, fungi), but may also be derived from a DNA or RNA virus. The selectable marker may be operative in prokaryotes and/or eukaryotes, and confer resistance to antibiotics such as, for example: ampicillin, hygromycin, kanamycin, neomycin, puromycin, tetracycline, or the like.

By appropriate manipulations, such as restriction, digesting back or filling in overhangs to provide blunt ends, ligation of linkers, or the like, complementary or flush ends of the fragments can be provided for joining and ligation.

In carrying out the various steps, cloning is employed, so as to amplify the amount of DNA and to allow for analyzing the DNA to ensure that the gene manipulations have occurred in a proper manner. A wide variety of cloning vectors are available, where the cloning vector includes a replication system functional in *E. coli* and a marker which allows for selection of the transformed cells. Illustrative vectors include pBR332, the pUC series, the M13 mp series, pACYC184, etc. Thus, the sequence may be inserted into the vector at an appropriate restriction site(s), the resulting plasmid used to transform the *E. coli* host, the *E. coli* grown in an appropriate nutrient medium, the cells harvested and lysed, and the plasmid recovered. Analysis may involve sequence analysis, restriction analysis, induction of expression, electrophoresis, or the like. After each manipulation, the DNA sequence to be used in the final construct may be restricted and joined to the next sequence, where each of the partial constructs may be cloned in the same or different plasmids.

Depending upon the manner of introduction of the transcription construct into the host plant, other nucleotide sequences may be required. For example, when using the Ti- or Ri-plasmid for transformation of plant cells, as described below, at least the right border and frequently both the right and left borders of the T-DNA of the Ti- and Ri-plasmids will be joined as flanking regions to the transcription construct. The use of T-DNA for transformation of plant cells has received extensive study and is amply described in Fraley et al. (1986) and Lindsey (1996).

A variety of techniques are available for the introduction of nucleic acids into a plant cell host. These techniques include transformation with Ti-DNA employing *A. tumefaciens* or *A. rhizogenes* as the transforming agent, protoplast fusion, injection, electroporation, etc. (reviewed by Lindsey, 1996). For transformation with Arobacterium, plasmids can be prepared in *E. coli* which plasmids contain DNA homologous with the Ti-plasmid, particularly T-DNA. The plasmid may or may not be capable of replication in Arobacterium, that is, it may or may not have a broad spectrum prokaryotic replication system (e.g., RK290) depending in part upon whether the transcription construct is to be integrated into the Ti-plasmid or be retained on an independent plasmid. By means of a helper plasmid, the transcription construct may be transferred to *A. tumefaciens* and the resulting transformed organism used for transforming plant cells.

Conveniently, explants may be cultivated with *A. tumefaciens* or *A. rhizogenes* to allow for transfer of the expression cassette to the plant cells, the plant cells dispersed in an appropriate selective medium for selection, grown to callus, shoots grown and plantlets regenerated from the shoots by growing in rooting medium. The Agrobacterium host will contain a plasmid having the vir genes necessary for transfer of the T-DNA to the plant cells and may or may not have T-DNA. For injection and electroporation, disarmed Ti-plasmids (lacking the tumor genes, particularly the T-DNA region) may be used to introduce genes into the plant cell.

The cells which have been transformed may be grown into plants and either pollinated with the same transformed strain or different strains, and the resulting hybrid having the desired phenotypic characteristic identified. Two or more generations may be grown to ensure that the subject phenotypic characteristic is stably maintained and inherited and then seeds harvested to ensure the desired phenotype or other property has been achieved.

As a host cell, any plant variety may be employed which provides a seed of interest. Thus, for the most part, plants will be chosen where a seed-specific product of interest is involved. Seeds of particular interest include the oil seeds, such as from Arabidopsis, Brassica, cotton, soybean, safflower, sunflower, tobacco, flax, peanut, or the like. Seeds of species such as wheat, maize, or rice may also be of interest.

The nucleotide sequence that comprises the promoter of this invention contains more than 2000 nucleotides. Based on the analysis of other plant promoters it seems likely that a substantially smaller region of sequence contained within the promoter of this invention would exhibit similar properties. For instance, as noted above, a 152 bp fragment from the napin promoter directed strong expression of the β-glucuronidase reporter gene in *B. napus* and tobacco seeds (Stalberg et: al., 1996). Thus, we envision that a subsequence of a few hundred nucleotides or less may be found to have the same or similar properties as the full sequence disclosed here.

This subsequence may be identified by the kinds of experiments exemplified in the work of Stalberg et al. (1996) and others, such as those cited in the review by Bevan et al. (1993). The minimal promoter sequence can be identified by successively removing nucleotides from the promoter sequence (i.e. truncation) and comparing the activity of the modified promoter with that of the native promoter. In addition, linker scanning or saturation mutagenesis may be used to produce the modified promoter. The promoter activity that may be assayed include, for example, the amount of transcription, the temporal specificity of transcription (i.e., early), the spatial specificity of transcription (i.e., seed), or a combination thereof of the kappa hydroxylase promoter. In a similar manner, enhancer or silencer sequences may be identified and modified. An enhancer or silencer sequence would not determine the position of transcription initiation, but could function in either orientation relative to the promoter and could be located at some distance from the promoter; an enhancer would increase transcription from an operably linked promoter and a silencer would decrease transcription from an operably linked promoter, presumably due to the presence of a cognate binding factor that recognizes the enhancer or silencer sequence. An enhancer binding factor would be expected to be present in early seed tissues whereas a silencer binding factor would be expected to be present in tissues other than seed or at times other than early development. The promoter, enhancer, silencer, or a combination thereof may be responsible for early seed-specific transcription by the kappa hydroxylase regulatory region. The promoter, enhancer, and/or silencer modules identified by genetic manipulation may be combined with native sequences or heterologous regulatory sequence from other genes, preferably plant genes.

Computer comparison of 5' untranslated regions that are conserved between different plant fatty acyl hydroxylase genes may also be used to identify transcription regulatory regions (Gribskov and Devereux, 1991). Regulatory regions may also be identified by searching for consensus sequences that would be recognized by a known transcription binding factor, often such consensus sequences will exhibit dyad symmetry. The function of such putative regulatory regions may be confirmed by gel retardation or nuclease protection.

An assay for identifying a transcription regulatory region will typically involve fusing the region to a suitable reporter gene, such as the E. Coli β-glucuronidase, then introducing that reporter construct into transgenic plants and assaying the amount of β-glucuronidase activity, protein, or mRNA produced (see Gallagher, 1992). Other reporter genes may be used, for example, alkaline phosphatase, chloramphenicol acetyltransferase, luciferase, β-galactosidase, green fluorescent protein, or derivatives thereof. Preferably, the assays are performed on stably transformed plants, but useful information may sometimes be gained by assaying tissues which have been transiently transformed with the constructs by particle bombardment or the like. Thus, many derivatives of the regulatory region disclosed herein are envisioned which would have similar or equal levels of activity. In addition, it is envisioned that many nucleotide changes in the sequence of the transcription regulatory region or a derivative, will have equivalent activity. Thus, deletions, insertions, inversions, and/or substitutions in the disclosed nucleotide sequence may produce derivatives of the regulatory region with similar biological activity (e.g., amount of transcription, early transcription, seed-specific transcription). Preferably, a functionally equivalent derivative of SEQ ID NO:1 would comprise at least 2000 bp, at least 1600 bp, at least 1400 bp, at least 1200 bp, at least 1000 bp, at least 800 bp, at least 600 bp, at least 400 bp, at least 200 bp, at least 100 bp, or at least 50 bp.

The following examples are offered by way of illustration and not by way of limitation.

EXAMPLES

Abbreviations: X-Gluc (5-Bromo-4-chloro-3-indolyl-β-D-glucuronic Acid) and GUS (β-glucuronidase).

MATERIALS AND METHODS

Cloning Vectors

Figure 2:
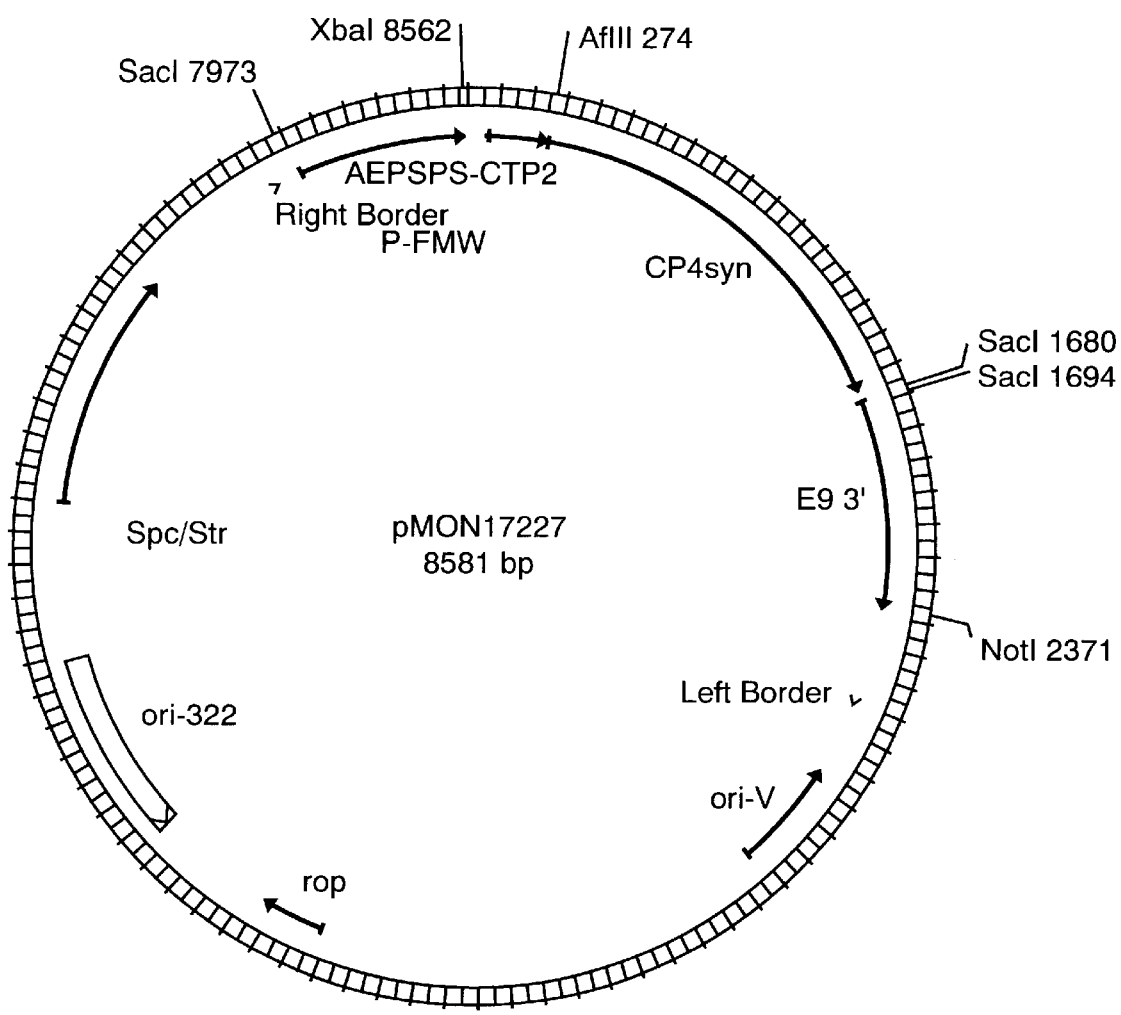
FIG. 2 is a restriction map of plasmid pMON17227.

The binary Ti plasmid pBI121 was purchased from Clontech (Palo Alto, Calif.). The ColE1-derived vector pMON26112 was obtained from Monsanto and is shown in FIG. 1. This plasmid, which contains the napin promoter from *Brassica napus*, replicates in *E. coli* where it confers ampicillin resistance. The binary Ti plasmid pMON17227 (FIG. 2) contains an origin of replication from pBR322 to permit replication in *E. coli*, a spectinomycin/streptomycin resistance gene for selection in bacterial hosts and the left and right borders of the Ti plasmid flanking the CP4 synthase gene for selection on glyphosate and a NotI cloning site upstream of the nopaline synthase gene terminator sequence. The plasmid pMON17227-pLesq-GUS is a binary Ti plasmid derived from pMON17227 as described below.

Measurement of GUS Activity

The protocol for detecting GUS activity was as follows. Tissues were incubated in staining buffer (50 mM $KPO_4$ buffer pH 7.0 containing 20% methanol, 0.5% Triton X-100, 1 mM potassium ferrocyanide, 1 mM potassium ferricyanide and 3 mM X-Gluc). Typically, the tissue was incubated in this solution for about 12 hours but, in some cases where the staining was strong, the tissue was removed sooner and staining was completed in a shorter time. Samples were placed in a vacuum chamber at 650 mm Hg for 2 min then incubated for 15 hours at 37° C. Following staining, samples were cleared by successive 5 min immersions in 20%, 40%, 60% and 70% ethanol.

GUS activity was quantitated visually as follows: non-activity was scored as 0, the highest level of GUS activity observed was scored as 4 with a quasi-logarithmic scale. Samples that were approximately 50% as darkly stained as those given a rating of 4, were rated as 3; samples that were approximately 50% as darkly stained as those given a rating of 4, were rated as 3; samples that were approximately 50% as darkly stained as those given a rating of 3, were rated as 2; and samples that were approximately 50% as darkly stained as those given a rating of 2, were rated as 1.

Example 1

Seed-Specific Expression of Foreign Genes in Transgenic Arabidopsis Thaliana Isolation of a Seed-Specific Promoter from *L. fendleri*

Genomic DNA was prepared from young leaves of *L. fendleri* as described by Murray and Thompson (1980). A Sau3AI-partial digest genomic library constructed in the vector XDashII (Stratagene, La Jolla, Calif.) was prepared by partially digesting 500 μg of DNA, size selecting the DNA on a sucrose gradient (Sambrook et al., 1989), and ligating the DNA (12 kb average size) to the BamHI-digested arms of λDashII. The entire ligation was packaged according to the manufacturer's conditions and plated on *E. coli* strain XL1-Blue MRA-P2 (Stratagene). This yielded $5 \times 10^5$ primary recombinant clones. The library was then amplified according to the manufacturer's instructions. A fraction of the genomic library was plated on *E. coli* XL1-Blue and resulting plaques (150,000) were lifted to charged nylon membranes (Hybond $N^+$, Amersham, Arlington Heights, Ill.), according to the manufacturer's recommendations. DNA was crosslinked to the filters under UV with a Stratalinker (Stratagene).

Several clones carrying genomic sequences corresponding to the *L. fendleri* hydroxylase were isolated by probing the membranes with a cDNA clone of the *L. fendleri* kappa hydroxylase carried on plasmid pLesq2 (described in U.S. patent application Ser. No. 08/530,862). The insert from plasmid pLesq2 was labeled with $^{32}p$ by random priming. The filters were prehybridized for 2 hours at 65° C. in 7% SDS, 1 mM EDTA, 0.25 M $Na_2HPO_4$ (pH 7.2), 1% BSA and hybridized to the probe for 16 hours in the same solution. The filters were sequentially washed at 65° C. in solutions containing 2×SSC, 1×SSC, 0.5×SSC in addition to 0.1% SDS. A 4.5 kb HindIII/NotI fragment containing the complete coding sequence for the hydroxylase and approximately 2.2 kb of the 5' upstream region was subcloned into the corresponding sites of pBluescript KS (Stratagene) to produce plasmid pLesqtot, and the sequence of the promoter region determined completely using an automatic sequencer by the dideoxy chain termination method. Sequence data was analyzed using the computer software package DNASIS (Hitachi, Brisbane, Calif.).

Partial sequence of the insert in clone pLesqtot is shown in FIG. 3 (SEQ ID NO:1). The sequence comprises 3670 bp of continuous DNA sequence. The clone encodes a 2217 bp untranslated region (i.e., nucleotides preceding the first ATG codon), an 1152 bp open reading frame, and a 302 bp 3' untranslated region. The open reading frame encodes a 384 amino acid protein with a predicted molecular weight of 44,370.

Construction of the Vector pBI101-pLesq-GUS and Transformation of Arabidopsis

Figure 4:
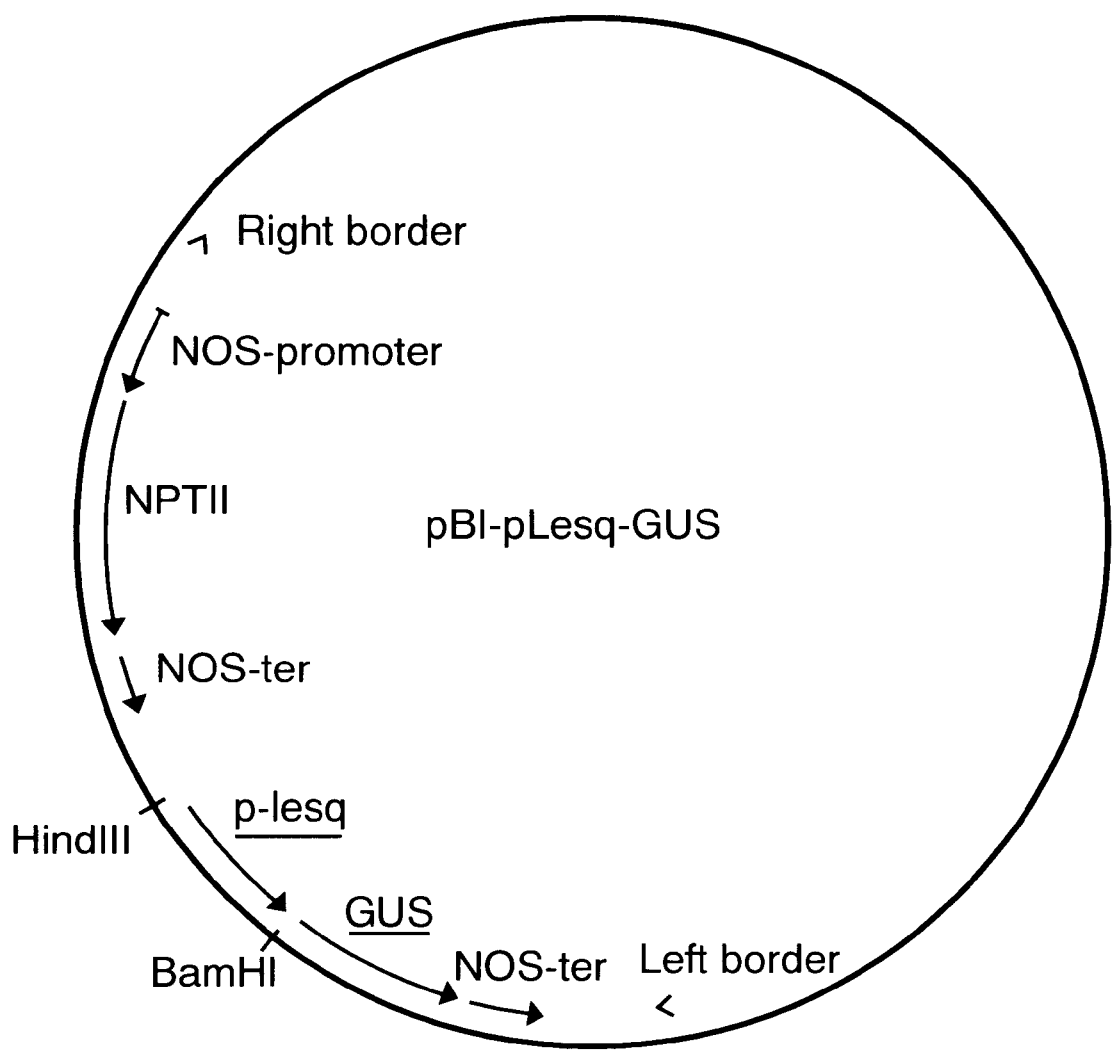
FIG. 4 is a restriction map of plasmid pBI-pLesq-GUS.

In a first step, pLesqtot was cut with HindIII and EcoRI, and a 2.2 kb insert fragment was cloned into pBluescript KS. The resulting vector, pLesqprom, contains 2.2 kb of sequence upstream of the ORF in pLesqtot. The promoter fragment did not contain a BamHI site but the polylinker of pBluescipt KS contains a BamHI site adjacent to the EcoRI cloning site. Thus, pLesqprom was then cut with HindIII and BamHI and the insert fragment purified by agarose gel electrophoresis. pBI121 was cut with the same enzymes to release the 35S promoter fragment. The HindIII/BamHI insert fragment of pLesqprom was then ligated into the corresponding sites of pBI121 to obtain the vector pBI-pLesq-GUS (FIG. 4). pBI-pLesq-GUS was then introduced into *Agrobacterium tumefaciens* strain GV3101 by electroporation, and used to transform Arabidopsis plants.

Cells for electroporation were prepared as follows. GV3101 was grown in LB medium (10 g tryptone, 5 g yeast extract, 5 g NaCl per liter of water). A 250 ml culture was grown to $OD_{600}=0.6$, then centrifuged at 4000 rpm (Sorvall GS-A rotor) for 15 min. The supernatant was aspirated immediately from the loose pellet, which was gently resuspended in 500 ml ice-cold water. The cells were centrifuged as before, resuspended in 30 ml ice-cold water, transferred to a 30 ml tube, and centrifuged at 5000 rpm (Sorvall SS-34 rotor) for 5 min. This was repeated three times, resuspending the cells consecutively in 30 ml ice-cold water, 30 ml ice-cold 10% glycerol, and finally in 0.75 ml ice-cold 10% glycerol. These cells were aliquoted, frozen in liquid nitrogen, and stored at −80° C.

Electroporation employed a GenePulser instrument (Bio-Rad, Hercules, Calif.) using cold 2 mm-gap cuvettes containing 40 $\mu$l of cells and 1 $\mu$l of DNA in water, at a voltage of 2.5 KV and capacitance of 25 $\mu$F. The electroporated cells were diluted with 1 ml SOC medium (Sambrook et al., 1989, page A2) and incubated at 28° C. for 2–4 hours before plating on LB medium containing kanamycin (50 mg/l).

Arabidopsis plants were transformed by the in planta transformation procedure essentially as described by Bechtold et al. (1993). Cells of *A. tumefaciens* GV3101 (pBI-pLesq-GUS) were harvested from liquid cultures by centrifugation, then resuspended in infiltration medium at $OD_{600}=0.8$. Infiltration medium was Murashige and Skoog macro and micronutrient medium (Sigma, St. Louis, Mo.) containing 10 mg/l 6-benzylaminopurine and 5% glucose. Batches of 12–15 plants were grown for 3 to 4 weeks in natural light at a mean daily temperature of approximately 25° C. in 3.5 inch pots containing soil. The intact plants were immersed in the bacterial suspension, then transferred to a vacuum chamber and placed under 600 mm of vacuum produced by a laboratory vacuum pump until tissues appeared uniformly water-soaked (approximately 10 min). The plants were grown at 25° C. under continuous light (100 $\mu$mol m$^{-2}$ s$^{-1}$ irradiation in the 400 to 700 nm range) for four weeks. The seeds obtained from all the plants in a pot were harvested as one batch. The seeds were sterilized by sequential treatment for 2 min with ethanol followed by 10 min in a mixture of household bleach (Chlorox), water and Tween-80 (50%, 50%, and 0.05%), then rinsed thoroughly with sterile water. The seeds were plated at high density (2000 to 4000 per plate) onto agar-solidified medium in 100 mm petri plates containing ½ X Murashige and Skoog salts medium enriched with B5 vitamins (Sigma) and containing kanamycin at 50 mg/l. After incubation for 48 hours at 4° C. to stimulate germination, seedlings were grown for a period of seven days until transformants were clearly identifiable as healthy green seedlings against a background of chlorotic kanamycin-sensitive seedlings. The transformants were transferred to soil and grown to maturity. More than 20 transformants were obtained.

Analysis of Transgenic Plants

The activity of the kappa hydroxylase promoter was assayed by staining various tissues of the transgenic Arabidopsis plants for the presence of β-glucuronidase activity by staining with X-Gluc (5-bromo-4-chloro-3-indolyl-β-D-glucuronic acid). Histochemical staining was carried out on leaves, stems, siliques, flowers and developing embryos isolated at different stages from transgenic Airabidopsis plants. Arabidopsis embryos from three transgenic plants were dissected out of their seedcoat, and staged from late-heart stage to late-cotyledon stage on plates containing MS-salts medium with 7.5 g/l agar, before being transferred to GUS staining buffer. Leaves, stems, and inflorescences were collected from transgenic plants and directly immersed in staining buffer.

The results obtained with three independent transgenic plants, designated 1 to 3, is shown in Table 1. It can be seen from these results that the kappa hydroxylase promoter caused the appearance of GUS activity as early as the torpedo stage embryo. The GUS activity persisted throughout subsequent development of the embryo. The amount of GUS activity in pBI-pLesq-GUS transgenic plants was compared with transgenic plants expressing the GUS gene driven by the promoter from the gene encoding the alpha subunit of the soybean beta-conglycinin (7S) gene (Hirai et al., 1994). p7S-GUS plants were chosen for their high level of GUS expression. The Lesquerella promoter was active earlier than the 7S promoter. Onset of activity coincides with that of storage lipid accumulation in Arabidopsis (Table 1). The level of GUS activity in the transgenic plants containing the kappa hydroxlase promoter was at least as high as in the transgenc plants containing the soybean β-conglycinin promoter. There was no GUS activity in samples of leaves, stems, or pods of the transgenic plants. Thus, the kappa hydroxylase promoter can be used to cause seed-specific expression of foreign genes in transgenic plants.

Table 1. Histochemical staining of transgenic Arabidopsis plants expressing the GUS gene under the control of different seed-specific promoters

TABLE 1

Histochemical staining of transgenic Arabidopsis plants expressing the GUS gene under the control of different seed-specific promoters.

| | A | B | C | E1 | E2 | E3 | E4 | E5 | F |
|---|---|---|---|---|---|---|---|---|---|
| Lesquerella kappa hydroxylase promoter | | | | | | | | | |
| 1 | 0 | 0 | 0 | 0 | 1 | 2 | 4 | 4 | 1 |
| 2 | 0 | 0 | 0 | 0 | 1 | 2 | 4 | 4 | 1 |
| 3 | 0 | 0 | 0 | 0 | 1 | 2 | 4 | 4 | 1 |
| Soybean beta-conglycinin promoter (alpha subunit) | | | | | | | | | |
| 1 | 0 | 0 | 0 | 0 | 0 | 0 | 2 | 4 | 0 |
| 2 | 0 | 0 | 0 | 0 | 0 | 0 | 2 | 4 | 0 |
| 3 | 0 | 0 | 0 | 0 | 0 | 0 | 2 | 4 | 0 |

A: leaf
B: stem
C: pod
E1: embryo (heart stage)
E2: embryo (torpedo stage)
E3: embryo (cane-shaped embryo)
E4: embryo (early cotyledon stage)
E5: mature embryo
0: no detectable staining
4: highest intensity of staining detected among samples of the same tissue type
3: intensity of staining about ½ of the maximum intensity
2: intensity of staining about ¼ of the maximum intensity
1: light staining, about 1/10 of the maximum intensity

Example 2

Seed-Specific Expression of Foreign Genes in Transgenic *Brassica Napus*

Construction of the Vector pMON17227-pLesq-GUS for Transformation of Canola

Figure 5:
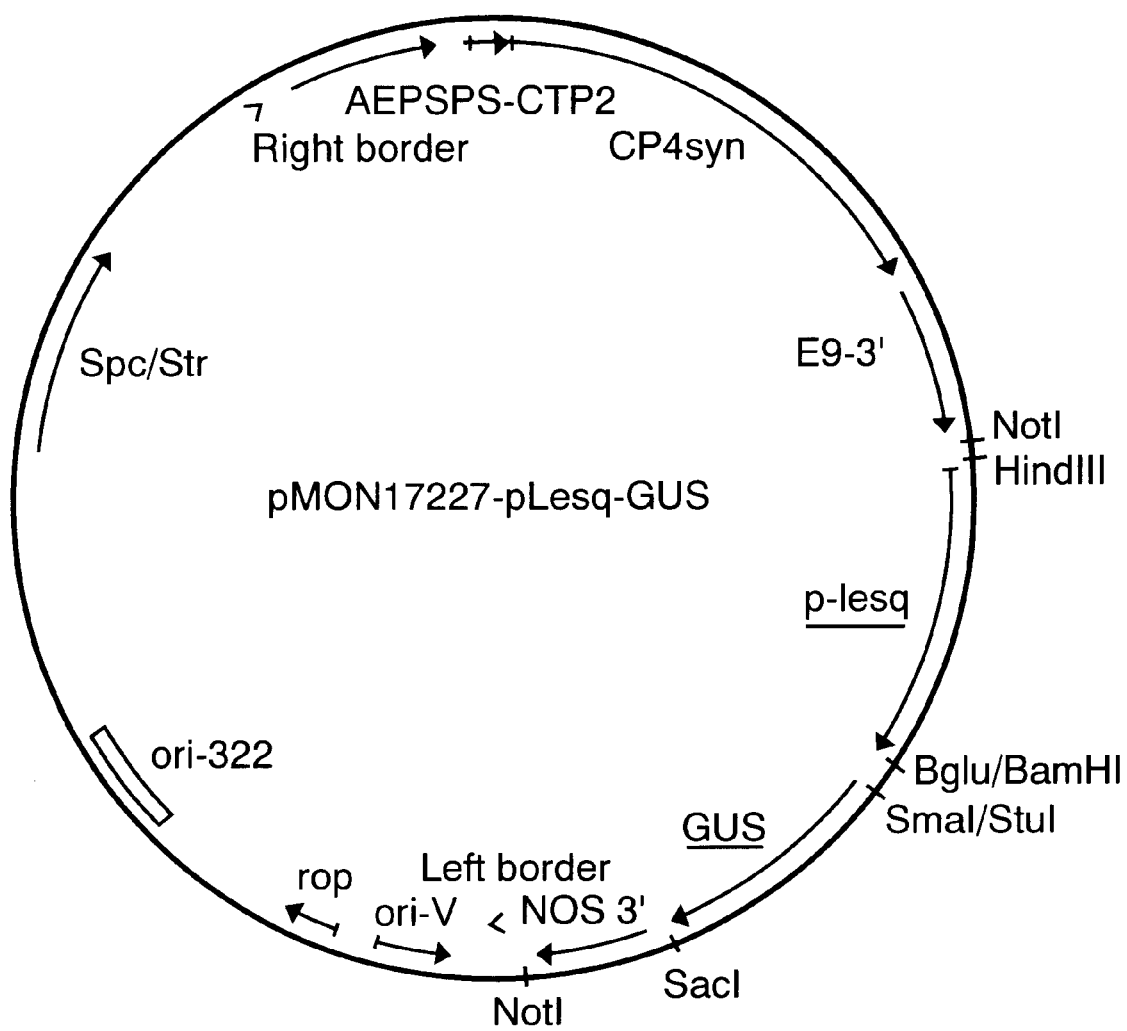
FIG. 5 is a restriction map of pMON17227-pLesq-GUS.

In a first step, the GUS gene was purified by cutting the vector pBI121 (Clontech) with SmaI and SacI. The insert fragment containing the GUS gene was cloned into the StuI and SacI sites of vector pMON26112, resulting in the vector pMON26112-GUS. In a second step, a HindIII/BamHI fragment from pLesqprom containing the *L. fendleri* kappa hydroxylase promoter was cloned into pMON26112-GUS cut with HindIII and BglII. The resulting vector (pMOEf26112-pLesq-GUS) was cut with NotI, and the insert fragment ligated to the vector pMON17227 cut with NotI. The final vector, pMON17227-pLesq-GUS (FIG. 5) was used to introduce the Lesquerella promoter-GUS cassette into canola plants using Agrobacterium-mediated transformation.

Transformation and Regeneration of *B. napus*

Agrobacterium strain ABI containing pMON17227-pLesq-GUS was used to transform *Brassica napus* cv Westar essentially as described by Fry et al. (1987). Briefly, seedlings are planted in Metro Mix 350 and grown in a growth chamber with these conditions: temperature day 15° C. and night 10° C., light intensity 600 $\mu$mol m$^{-2}$s$^{-1}$, 8 hours night, relative humidity 50%, and are transferred into 6 inch pots when they are 3 weeks old. Five-week-old Westar plants are harvested once the plants bolt, but prior to flowering (plants with up to 3 flowers may be harvested). The leaves and buds are removed and the 4–5 inches of stem below the flower buds are used as the explant tissue source. Just prior to inoculation, the stems are sterilized as follows: soak in 70% ethanol for 1 minute, soak in 38% Clorox for 20 minutes, rinse two times in sterile deionized water, and soak in two tablespoons of Captan 50-WP (ICI) plus 500 ml sterile water for 15 minutes.

Agrobacterium Preparation

Agrobacterium is streaked onto an LB plate containing spectinomycin 100 mg/l, Streptomycin 100 mg/l, chloramphenicol 25 mg/l, and kanamycin 50 mg/l (denoted LB-SSCK). Two days before inoculation, a 10 $\mu$l loop of Agrobacterium is placed into a tube containing 2 mls of LB-SSCK and put onto a rotator to grow overnight. The day before inoculation, the Agrobacterium is subcultured, 200 $\mu$l is placed in 2 ml of fresh LB-SSCK and returned to the rotator to grow overnight. On the inoculation day, the Agrobacterium is diluted 1:10 with MS liquid medium. An $OD_{600}$ reading is taken, readings in the range of 0.2 to 0.4 are acceptable.

Explant Inoculation

Stems are cut into one quarter inch segments, noting the basal orientation of the stems. Explants are inoculated in a petri plate for 5 minutes with the 1:10 dilution of Agrobacterium; 5 ml Agrobacterium per 5 stems are used and the Agrobacterium is pipetted directly on top of the explants. Agrobacterium is aspirated off of the explants after the 5 minute inoculation time. Stem explants are cultured in the basal-side down orientation for an optimal shoot regeneration response on the co-culture plates, (1/10 MS medium with a 2 ml TXD liquid medium covered with sterile 8.5 cm filter paper). TXD medium contains 4.3 g Gibco MS medium, 2 ml of 500×solution of Gamborg B5 mixture (Sigma), 8 ml p-chlorophenoxyacetic acid (0.5 mg/ml) 0.01 ml Kinetin (0.5 mg/ml), 30 g sucrose and water to one liter. Co-culture plates are put in clear plastic bags which are slit and placed at 25° C., 24 hours continuous cool-white light.

Tissue Selection and Regeneration

After a 2 day co-culture period, stem explants are moved onto MS medium containing 500 mg/l ticarcillin, 50 mg/l cefotaxime, and 1 mg/l benzylaminopurine (BAP) fer a 3 day delay period; again plates are put in clear plastic bags which are slit and placed at 25° C., 24 hours continuous cool-white light. After a three-day delay period, stern explants are moved onto MS 0.1 mM glyphosate selection medium containing glyphosate and the abovementioned levels of ticarcillin, cefotaxime, and BAP for three weeks. Then, the stem explants are moved onto the MS 0.1 mM glyphosate selection medium containing the same amounts of ticarcillin, cefotaxime, and BAP cited above plus 0.5 mg/l gibberellin (GA$_3$) which was found to enhance shoot elongation, for another three week period. After these six weeks on glyphosate selection medium, green, normal developing shoots are excised from the stem explants. Shoots (4–5 shoots per plate) are placed in rooting medium [Gibco MS salts, vitamins, 3% sucrose containing the above levels of ticarcillin and cefotaxime and 2 mg/l indolebutyric acid (IBA)]. Root development begins to occur as early as one week after shoots go onto rooting medium. At the 2 week timepoint, shoots with a large root base are moved into 2½ inch pots with potting soil (Metro Mix 350); flats are covered with the clear plastic domes so the shoots can elongate. All plants are placed in a growth chamber with the same conditions as described above for stock plant growth. When shoots are hardened off after 3–4 days, the plastic domes are cracked and several days later removed completely. The plants are grown in a growth chamber at 22° C. in a 16 hr/8 hr light/dark cycle with light intensity 220 $\mu$E m$^2$ S$^{-1}$ and after several weeks are transferred to the greenhouse.

Analysis of Transgenic Plants

Eighteen regenerated *B. napus* plants were examined for embyro-specific expression of the GUS gene using the same scale for expression levels as described in Example 1. Transgenic canola pods and seeds were collected at less than 10, 10, 16, 21, 28, 35 dpa and at maturity. Leaf, stem, pods and seed samples were stained for β-glucuronidase activity as described above. The results of the GUS assays are presented in Table 2.

Table 2. Histochemical staining of transgenic *B. napus* plants expressing the GUS gene under the control of different seed-specific promoters.

TABLE 2

Histochemical staining of transgenic *B. napus* plants expressing the GUS gene under the control of different seed-specific promoters.

| | A | B | C | D1 | D2 | D3 | D4 | D5 | D6 | D7 |
|---|---|---|---|---|---|---|---|---|---|---|
| 1 | 0 | 0 | 0 | | | | | | 1 | 1 |
| 2 | 0 | 0 | 0 | 3-4 | 3-4 | | | | 2 | 0 |
| 3 | 0 | 0 | 0 | 3-4 | 3-4 | | | | 1 | 1 |
| 4 | 0 | 0 | 0 | 3-4 | 3-4 | 3-4 | 3-4 | | 1 | 0 |
| 5 | 0 | 0 | 0 | 3-4 | 3-4 | | | | 1 | 1 |
| 6 | 0 | 0 | 0 | | | | | | 1 | 0 |
| 7 | 0 | 0 | 0 | 3-4 | 3-4 | | | | 1 | 0 |
| 8 | 0 | 0 | 0 | 3-4 | 3-4 | 3-4 | 3-4 | 3-4 | | |
| 9 | 0 | 0 | 0 | 1 | 2 | | | | 1 | 0 |
| 10 | 0 | 0 | 0 | 2 | 2 | 2 | | | | |
| 11 | 0 | 0 | 0 | 2 | 3-4 | | | | | |
| 12 | 0 | 0 | 0 | 3-4 | 3-4 | | | | | |
| 13 | 0 | 0 | 0 | 3-4 | 3-4 | 3-4 | 3-4 | 4 | 2 | 1 |
| 14 | 0 | 0 | | 3-4 | | | | | | |
| 15 | 0 | 0 | 0 | | 3-4 | | | | | |
| 16 | 0 | 0 | 0 | 3-4 | 3-4 | | | | | |
| 17 | 0 | 0 | 0 | 3-4 | 3-4 | | | | | |
| 18 | 0 | 0 | 0 | 3-4 | 3-4 | | | | | |

A: leaf
B: stem
C: pod
D1: seed 16 dpa
D2: seed 21 dpa
D3: seed 28 dpa
D4: seed 35 dpa
D5: mature seed
D6: seed: <10 dpa
D7: seed: 10 dpa It is apparent from the results in Table 2 that a foreign gene fused to the kappa hydroxylase promoter is not expressed at significant levels in non-seed tissues, but is abundantly expressed in developing seeds. High levels of GUS staining were apparent as early as 16 days post-anthesis and the staining persisted throughout seed development. Thus, the kappa hydroxylase promoter is a useful promoter for causing the expression of foreign genes in plants. The promoter is particularly useful in applications where it is desirable to have the gene of interest transcribed at high levels an early stage of seed development and persist throughout seed development. Such applications include modification of seed lipid metabolism.

All publications and patent applications mentioned in this specification are indicative of the level of skill of those skilled in the art to which this invention pertains.

All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious to the skilled artisan that certain changes and modifications may be practiced within the scope of the appended claims.

REFERENCES

Bechtold, N., Ellis, J., Pelletier, G. (1993) In planta Agrobacterium-mediated gene transfer by infiltration of adult *Arabidopsis thaliana* plants. C. R. Acad. Sci. Paris 316, 1194–1199.

Bevan, M., Colot, V., Hammond-Kossack, M., Holdsworth, M., Torres de Zabala, M., Smith, C., Grierson, C., Beggs, K. (1993) Transcriptional control of plant storage protein genes. Phil. Trans. Royal Soc. Lond. Biol. Sci. 342, 209–215.

Chen, Z. L., Pan, N. S., Beachy, R. N. (1988) A DNA sequence element that confers seed-specific enhancement to a constitutive promoter. EMBO J. 6, 3559–3564.

Fraley, R., Rogers, S., Horsch, R. B. (1986) Genetic transformation in higher plants. Crit. Rev. Plant Sci. 4, 1–46.

Fry et al., (1987) Transformation of *Brassica napus* with *Agrobacterium tumefaciens* based vectors. Plant Cell Reports 6, 321–325.

Gallagher, S. R. (1992) GUS Protocols. Academic Press, San Diego.

Gribskov, M., Devereux, J. (1991) *Sequence Analysis Primer*. Stockton Press, New York.

Hirai, M. Y., Fujiwara, T., Goto, K., Komeda, Y., Chino, M., Naito, S. (1994) Differential regulation of soybean seed storage protein gene promoter-GUS fusions by exogenously applied methionine in transgenic *Arabidopsis thaliana*. Plant Cell Physiology 35, 927–934.

Lindsey, K. (1996) Plant transformation systems. In *Transgenic Plants: A Production System for Industrial and Pharmaceutical Proteins*. Owen, M. R. L., Pen, J. (Eds.) Wiley, New York, pp. 5–25.

Murray, M. G., Thompson, W. F. (1980) Rapid isolation of high molecular weight plant DNA. Nucl. Acids Res. 8, 4321–4325.

Post-Beittenmiller, D., Ohlrogge, J., Somerville, C. R. (1992) Regulation of plant lipid biosynthesis: An example of developmental regulation superimposed on a ubiquitous pathway. In Control of Plant Gene Expression. Verma, D. P. (Ed.) Telford Press, pp. 157–174.

Sambrook, J., Fritsch, E. F., Maniatis, T. (1989) *Molecular Cloning: A Laboratory Manual*, 2nd Ed., Cold Spring Harbor Laboratory Press.

Stalberg, K., Ellerstoem, M., Ezcurra, I., Ablov, S., Rask, L. (1996) Disruption of an overlapping E-box-ABRE motif abolished high transcription of the napA storage-protein promoter in transgenic *Brassica napus* seeds. Planta 199, 515–519.

Voelker, T. A., Hayes, T. R, Cranmer, A. M., Turner, J. C., Davies, H. M (1996) Genetic engineering of a quantitative trait: Metabolic and genetic parameters influencing the accumulation of laurate in rapeseed. Plant Journal 9, 229–241.

What is claimed is:

1. An isolated nucleic acid comprising a transcription regulatory region, wherein said transcription regulatory region is nucleotide 1 to nucleotide 2214 of SEQ ID NO:1 and said isolated nucleic acid is a strong early seed-specific promoter.

2. A recombinant nucleic acid comprising the nucleic acid according to claim 1 and a heterologous gene.

3. The recombinant nucleic acid according to claim 2 wherein the heterologous gene is an enzyme of lipid metabolism.

4. The recombinant nucleic acid according to claim 3 wherein the heterologous gene is a plant hydroxylase gene.

5. A host plant cell comprising the recombinant nucleic acid according to claim 4.

6. An expression construct comprising a transcription regulatory region from claim 1 and a transcription termination region.

7. The expression construct according to claim 6 Wherein the transcription regulatory region is from a *Lesquerella fendleri* kappa hydroxylase gene.

8. The expression construct according to claim 6 further comprising a translation initiation region and a translation termination region.

9. The expression construct according to claim 6 further comprising a coding sequence for a plant kappa hydroxylase gene.

10. The expression construct according to claim 6 further comprising a coding sequence for a heterologous gene.

11. The expression construct according to claim 10 wherein the heterologous gene is an enzyme of lipid metabolism.

12. The expression construct according to claim 10 wherein the heterologous gene is operably linked to the transcription regulatory region and the transcription termination region such that a sense transcript of the heterologous gene would be produced.

13. The expression construct according to claim 6 wherein the transcription regulatory region is a promoter.

14. A microbial or a plant host cell comprising the expression construct according to claim 6.

15. The cell according to claim 14, wherein the host cell is a host plant cell.

16. A host plant cell comprising the expression construct according to claim 10.

17. The host plant cell according to claim 16 wherein the host plant cell is a Brassica species.

18. The host plant cell according to claim 16 wherein the host plant cell is a dicotyledenous species.

19. A process of altering fatty acid composition of a seed comprising:
(a) transforming a host plant cell with the recombinant nucleic acid according to claim 3,
(b) regenerating a transformed host plant,
(c) obtaining seed from a collection of transformed host plants, and
(d) screening the seeds for a desired composition of fatty acid.

\* \* \* \* \*

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 3670 nucleotides
      (B) TYPE: nucleic acid
      (C) STRANDEDNESS: single
      (D) TOPOLOGY: linear (xi) SEQUENCE DESCRIPTION: SEQ ID NO:1:

```
AAGCTTTTGA GCTCATCAGT TACTCAGGAA GATTAAGTCT                           40

TTGCTTGTTG TCTGATTTTC TTTAAATACA TGAAGGATCG                           80

GTTATGAATC TTCTTTTTTT GTGTTTTGGG ATTATGAAGC                          120

TGTCTTTGGA TATTAGTTGC GGTTATTAGC ATGCTTCTCT                          160

TTTGTGTTTT GGGGATTATG AAGCAGGGTC TGTCTATGTA                          200

ATGCATTTTG TTTGAAAACT CAGCTAATGC TAATGCAATT                          240

TCTTTTGAAA CCTTTGTTAT GTTTTCGAAA ATATTGAATA                          280

NGTTCTGTTA TGGATTTATT TGCAAAAGCC ATTGATTAAA                          320

TCAAACATTA CATAAGAACA ACATTCATTA TTAACTAATT                          360

AGAGATGCAA AACACAACAT TACATACAAC ATCAGTGACT                          400

AATTATTGAG ACAAAACAAC ATCACATACA CAAACATTCA                          440

TCTCATACAT CACTTAGAGA GACACAAAAA GCAACCAAAC                          480

ACAACTATTC CGGCAACAAC AATTAGCTTC ATACGTTTTG                          520

CTTCTCCTTT CAAGCCTTCA ATCATCTTCT CACAGCCACG                          560

AATCTGAGCC TTCAATAATA ACATTTCTTC ATCGTGACAC                          600

TTCTCACGGT TATGAATGTA AGCCTTTATG TCCTCTACTT                          640

CTTCTACTAA AGACACATCA GTCCACTTCC AGGTGTGGAA                          680

TCCTCCTCTT TTGAAATTTT TCTCACAGGT ATGGAATAAT                          720

CTACCTAGGT TTTTTGGAGT TCTTGAGGTT CTGATCACAA                          760

CACGACATCC AAATCGACAG GTCTTAGGAA AACCACGATG                          800

GTTATCATCT TCAAGCTCAC TGTCAAAAGA GAAAAACGAG                          840

TTTGAAGAAG AAGAAGGCAT TATCAATTTC AGAGAATTTT                          880

GGAGAATTTT GAGAGATTGA GAATTGGGAA ATAAGAACCC                          920

TAATCCCCAA TTTATGAGAT TGAAAATATA TCCGTTAGAG                          960

AAGAAACATA ATGCTGTGCG TTTTAATTAG AAAAAATAGA                         1000

GATGGGCTTT ATCTTTTGTT AAGAGTTTTG GGCTTGGGCT                         1040

TGGGTTTTTG ATAAAAAAAT TTAATTAAAC CAAAACGACG                         1080

TCGTTTGGTT TAATTGTTGT TAAAAAAAAT TAAAACACCA                         1120

AAACGACGTC GTTTTGGTGT TATTAACGGC CTTAAAACGG                         1160

ATTAAATCCA TAATCCGTCA GTCAACTAGG TTACGGATGG                         1200

TCAACGGCGT TTTTGCATAA CGGAGGCACA GTTCAGGCTT                         1240
```

| | |
|---|---|
| AACGGAGTGG ACCGAATGGC TTTTTAGGAA GTTTGTAACC | 1280 |
| GGGATTTTTT GTTTATGATG TATTTGTCCC CGTCGGCTAT | 1320 |
| TGTTTAGGCC GTTTTTCCTA TATATTGGAA ATAACTATTG | 1360 |
| TCCAGACGAG TTACTTCTCC AACATATCAA GAAATGTTAC | 1400 |
| AAAGAAGTGT TACAAAAATG TGTTACTAAG CCATAAAACT | 1440 |
| CAAAGCATAT ATCTTAGACC CTAAGCCTAA ACCCTAGAAC | 1480 |
| TTTCTAGGAC GTTTATACCT TGTCCTTTCT TTAGTTTCCT | 1520 |
| TTAAAGGCCT TCGTATTCAT AAGTTTTATT TTTGCTTAAT | 1560 |
| ACTAACACTA GAAATAATCA ACATAAACTA GGTTAAGTCG | 1600 |
| TGGATCTAAT TTTATTGTGA AAATGTAATT GCTTCTCTTA | 1640 |
| AGAAAGATT CATAGCAAAA TATTCGCATC TTTCTTGTGA | 1680 |
| ATCATCTTTT GTTTTTGGGG CTATTAAAGA AAAATTGAAC | 1720 |
| TCATGAAATG GTGACAACTT TATTCTAGAG GTAACAGAAC | 1760 |
| AAAAATATAG GAACAACACG TGTTGTTCAT AAACTACACG | 1800 |
| TATAATACTC AAGAAGATGA ATCTTTATAA GAATTTAGTT | 1840 |
| TTCTCATGAA AACATAAAAA ATTTTGTCAA TTGAAAGTGA | 1880 |
| CAGTTGAAGC AAAGGAACAA AAGGATGGTT GGTGATGATG | 1920 |
| CTGAAATGAA AATGTGTCAT TCATCAAATA CTAAATACTA | 1960 |
| CATTACTTGT CACTGCCTAC TTCTCCTATT TCCTCCGCCA | 2000 |
| CCCATTTTGG ACCCACGAGC CTTCCATTTA AACCCTCTCT | 2040 |
| CGTGCTATTC ACCAGAAGAG AAGCCAAGAG AGAGAGAGAG | 2080 |
| AGATTGTGCT GAGGATCATT GTCTTCTTCA TCGTTATTAA | 2120 |
| CGTAAGTTTT TTTTGACCAC TCATATCTAA AATCTAGTAC | 2160 |
| ATGCAATAGA TTAATGACTG TTCCTTCTTT TGATATTTTC | 2200 |
| AGCTTCTTGA ATTCAAGATG GGTGCTGGTG GAAGAATAAT | 2240 |
| GGTTACCCCC TCTTCCAAGA AATCAGAAAC TGAAGCCCTA | 2280 |
| AAACGTGGAC CATGTGAGAA ACCACCATTC ACTGTTAAAG | 2320 |
| ATCTGAAGAA AGCAATCCCA CAGCATTGTT TCAAGCGCTC | 2360 |
| TATCCCTCGT TCTTTCTCCT ACCTTCTCAC AGATATCACT | 2400 |
| TTAGTTTCTT GCTTCTACTA CGTTGCCACA AATTACTTCT | 2440 |
| CTCTTCTTCC TCAGCCTCTC TCTACTTACC TAGCTTGGCC | 2480 |
| TCTCTATTGG GTATGTCAAG GCTGTGTCTT AACCGGTATC | 2520 |
| TGGGTCATTG GCCATGAATG TGGTCACCAT GCATTCAGTG | 2560 |
| ACTATCAATG GGTAGATGAC ACTGTTGGTT TTATCTTCCA | 2600 |
| TTCCTTCCTT CTCGTCCCTT ACTTCTCCTG GAAATACAGT | 2640 |
| CATCGTCGTC ACCATTCCAA CAATGGATCT CTCGAGAAAG | 2680 |
| ATGAAGTCTT TGTCCCACCG AAAAAAGCTG CAGTCAAATG | 2720 |
| GTATGTTAAA TACCTCAACA ACCCTCTTGG ACGCATTCTG | 2760 |
| GTGTTAACAG TTCAGTTTAT CCTCGGGTGG CCTTTGTATC | 2800 |

-continued

| | |
|---|---|
| TAGCCTTTAA TGTATCAGGT AGACCTTATG ATGGTTTCGC | 2840 |
| TTCACATTTC TTCCCTCATG CACCTATCTT TAAAGACCGA | 2880 |
| GAACGCCTCC AGATATACAT CTCAGATGCT GGTATTCTAG | 2920 |
| CTGTCTGTTA TGGTCTTTAC CGTTACGCTG CTTCACAAGG | 2960 |
| ATTGACTGCT ATGATCTGCG TCTATGGAGT ACCGCTTTTG | 3000 |
| ATAGTGAACT TTTTCCTTGT CTTGGTAACT TTCTTGCAGC | 3040 |
| ACACTCATCC TTCGTTACCT CATTATGATT CAACCGAGTG | 3080 |
| GGAATGGATT AGAGGAGCTT TGGTTACGGT AGACAGAGAC | 3120 |
| TATGGAATAT TGAACAAGGT GTTCCATAAC ATAACAGACA | 3160 |
| CACATGTGGC TCATCATCTC TTTGCAACTA TACCGCATTA | 3200 |
| TAACGCAATG GAAGCTACAG AGGCGATAAA GCCAATACTT | 3240 |
| GGTGATTACT ACCACTTCGA TGGAACACCG TGGTATGTGG | 3280 |
| CCATGTATAG GGAAGCAAAG GAGTGTCTCT ATGTAGAACC | 3320 |
| GGATACGGAA CGTGGGAAGA AAGGTGTCTA CTATTACAAC | 3360 |
| AATAAGTTAT GAGGCTGATA GGGCGAGAGA AGTGCAATTA | 3400 |
| TCAATCTTTT TTTCATGTTT TAGGTGTCTT GTTTAAGAAG | 3440 |
| CTATGCTTTG TTTCAATAAT CTCAGAGTCC ATTTAGTTGT | 3480 |
| GTTCTGGTGC ATTTTGCCTA GTTATGTGGT GTCGGAAGTT | 3520 |
| AGTGTTCAAA CTGCTTCCTG CTGTGCTGCC CAGTGAAGAA | 3560 |
| CAAGTTTACG TGTTTAAAAT ACTCGGAACG AATTGACCAC | 3600 |
| AANATATCCA AAACCGGCTA TCCGAATTCC ATATCCGAAA | 3640 |
| ACCGGATATC CAAATTTCCA GAGTACTTAG | 3670 |